United States Patent
Shenoy et al.

(10) Patent No.: US 7,767,213 B2
(45) Date of Patent: Aug. 3, 2010

(54) SYNTHETIC NANOPORES FOR DNA SEQUENCING

(75) Inventors: Devanand K Shenoy, McLean, VA (US); Enrico Dalcanale, Parma (IT); Sander Willems, Parma (IT); Marco Busi, Parma (IT)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 66 days.

(21) Appl. No.: 12/357,557

(22) Filed: Jan. 22, 2009

(65) Prior Publication Data

US 2009/0131669 A1    May 21, 2009

Related U.S. Application Data

(62) Division of application No. 11/070,397, filed on Feb. 28, 2005, now Pat. No. 7,504,505.

(60) Provisional application No. 60/550,739, filed on Mar. 1, 2004, provisional application No. 60/559,288, filed on Mar. 31, 2004.

(51) Int. Cl.
 *A61K 9/00* (2006.01)
 *C07F 15/00* (2006.01)

(52) U.S. Cl. .......................................... 424/400; 546/2

(58) Field of Classification Search ................ 424/400; 546/2

See application file for complete search history.

(56) References Cited

OTHER PUBLICATIONS

Sun, S. et al.: Self-assembly triangular and square rhenium (I) tricarbonyl complexes: A comprehensive study of their preparation, electrochemistry, photophysics, photochemistry, and host-guest properties. J. Am. Chem. Soc., vol. 122, pp. 8956-8967, 2000.*

* cited by examiner

*Primary Examiner*—Charanjit S Aulakh
(74) *Attorney, Agent, or Firm*—Amy L. Ressing; Joseph T. Grunkemeyer

(57) ABSTRACT

A compound and methods of making thereof having the structure shown below is disclosed. Each Ar is an aromatic group. Each M is palladium, platinum, or rhenium. At least one X in the compound has an aliphatic having at least 1 carbon atom. Each x, each y, and each z is an integer greater than or equal to zero. Each m is an integer greater than or equal to one. n is an integer greater than or equal to three.

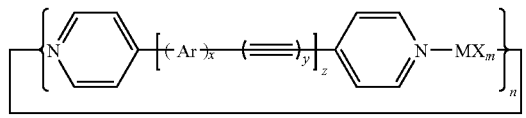

7 Claims, 2 Drawing Sheets

SYNTHETIC NANOPORES FOR DNA SEQUENCING

This application is a divisional application of U.S. patent application Ser. No. 11/070,397 filed on Feb. 28, 2005 and allowed, which claims priority to U.S. Provisional Patent Application No. 60/550,739 filed on Mar. 1, 2004 and to U.S. Provisional Patent Application No. 60/559,288 filed on Mar. 31, 2004, all incorporated herein by reference.

BACKGROUND OF THE INVENTION

1. Field of the Invention

The invention is related to cyclic oligomeric compounds.

2. Description of Related Art

There are two approaches in nanopore sequencing. In the first approach, the proteinaceous pore, alpha-Hemolysin, is used to reconstitute a planar phospholipid bilayer membrane. A black lipid membrane (BLM) is formed on a thin Teflon partition with a hole in the middle several tens of microns in diameter. The partition separates identical aqueous media (e.g. 1 M KCl with buffer at neutral pH) in a trough. A voltage is applied so as to drive an ionic current through the open pore.

If single stranded DNA is introduced into the cis chamber (the chamber with the negative electrode) current blockades are observed during polyanionic DNA translocation through the protein pore into the opposite trans chamber. (Henrickson et al., "Driven DNA Transport into an Asymmetric Nanometer-Scale Pore," *Phys. Rev. Lett.*, 85, 3057 (2000). All referenced publications and patent documents are incorporated herein by reference.) The limitations with this approach are that 1) proteins are fragile, 2) scaling tip for industrial production is not feasible 3) the nanopore is highly asymmetric in size and interactions 4) conformational fluctuations within the pore raise the noise level.

To eliminate the problems associated with fragile pores, solid state membranes (such as silicon nitride) were ion beam milled to form a pore for nanopore sequencing (Li et al., "DNA Molecules and Configurations in a Solid-State Nanopore Microscope," *Nature Mat.*, 2, 611(2003)). The disadvantages with this approach are 1) it is difficult to routinely process holes less than 40 nm in diameter 2) reproducibility of the pore features is difficult 3) the membrane thickness is much larger than the size of a DNA nucleotide 4) interaction between the translocating DNA and the pore cannot be tuned for controlling the translocation (other than through physical variables such as Voltage and concentration of solution).

SUMMARY OF THE INVENTION

The invention comprises a compound comprising the formula in Eq. (1). Each Ar is an independently selected aromatic group, heteroaromatic group, or polyaromatic group. Each M is independently selected from the group consisting of palladium, platinum, and rhenium. Each X is an independently selected chemical group or bidentate chelating ligand, with the proviso that at least one X in the compound comprises an aliphatic having at least 1 carbon atoms. Each x, each y, and each z is an independently selected integer greater than or equal to zero. Each m is an independently selected integer greater than or equal to one. n is an integer greater than or equal to three.

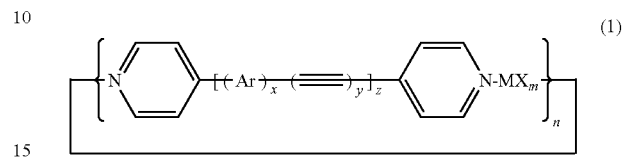

The invention further comprises a compound comprising the formula in Eq. (2). Ar, x, y, z, and m are as defined above. Z is an independently selected chemical group or bidentate chelating ligand. Each x', each y', and each z' is an independently selected integer greater than or equal to zero.

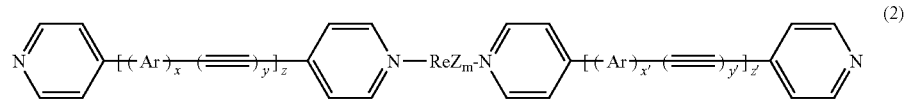

The invention further comprises a method of making a compound comprising providing a spacer compound comprising the formula in Eq (3) and reacting it with a metal compound comprising the formula $Y_2MX_m$. Ar, x, y, z, M, X, and m are as defined above. Each Y is an independently selected leaving group capable of facilitating the formation of a N-M bond with a pyridinyl nitrogen.

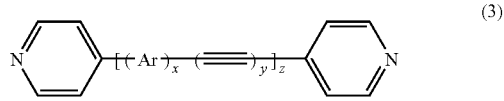

The invention further comprises a method of making a compound comprising providing a 90° angled compound comprising the formula in Eq. (2) and reacting it with a metal compound comprising the formula $Y_2MX_m$. X, m, and Y are as defined above. M is palladium or platinum.

BRIEF DESCRIPTION OF THE DRAWINGS

A more complete appreciation of the invention will be readily obtained by reference to the following Description of the Example Embodiments and the accompanying drawings.

DETAILED DESCRIPTION OF THE EXAMPLE EMBODIMENTS

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as not to obscure the description of the present invention with unnecessary detail.

The approach disclosed can utilize robust, synthetic organic nanopores to replace the fragile proteinaceous ion pores currently used for studying DNA translocation. The interaction forces between the translocating molecule and the organic nanopore may be tuned (theoretically predicted to control biomolecule translocation) by engineering the pore (size and chemistry) to achieve single base pair resolution.

Figure 1:
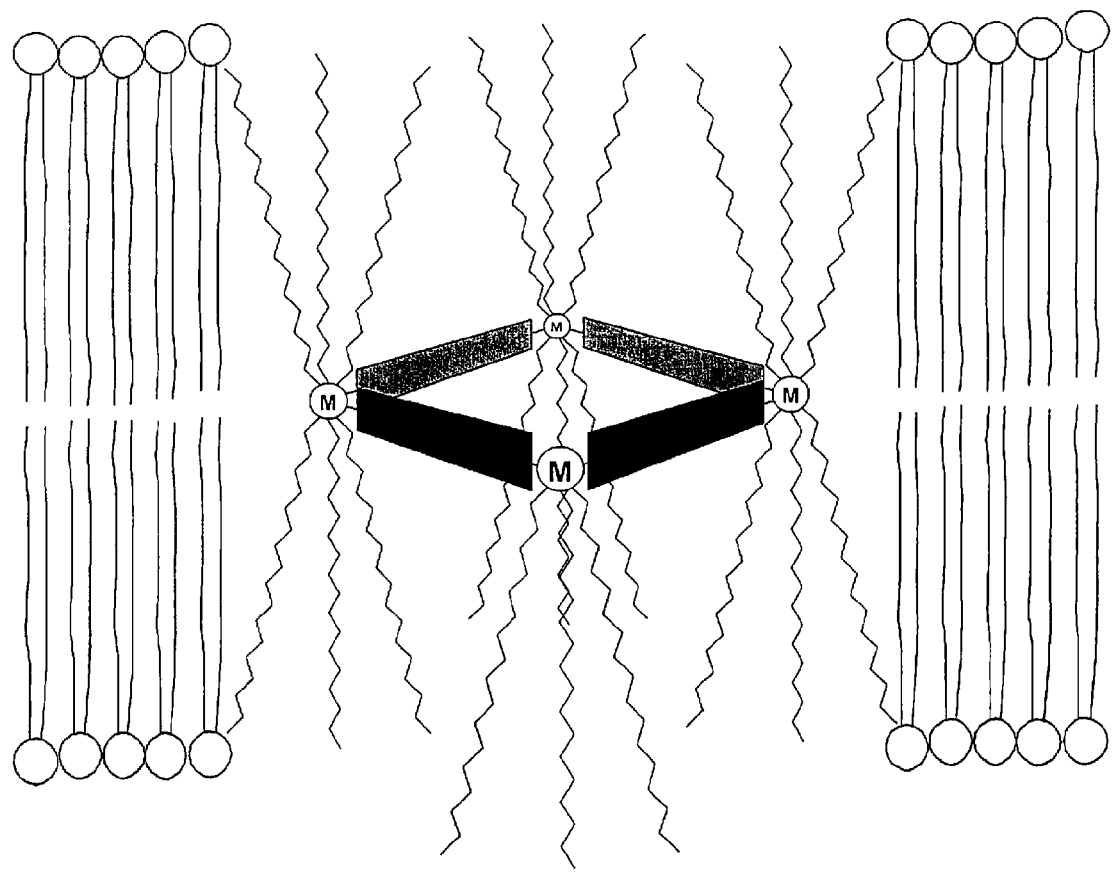
FIG. 1 schematically illustrates a compound of the invention in a lipid bilayer.

A nanoscale interface technology is schematically illustrated in FIG. 1. A bilayer lipid membrane 10 is reconstituted with the organic nanopore 20. This can form the partition in a nanopore sequencer to replace the delicate protein pores currently in use. The organic nanopore approach may afford the capability to fabricate nanopores at the size scale required for high resolution sequencing, for example, in the 1 to 2 nm range. It is currently impossible to routinely machine holes of that size in a silicon nitride membrane, for example.

Possible characteristics of the organic nanopores may include: 1) robust, 2) reproducible, 3) one-time synthesis is sufficient since a large number of pores are available even in a milligram of material, 4) amenable to industrial scale production, 5) provide a symmetric barrier, 6) size and chemistry can be varied to tune DNA pore interaction (rather than varying physical variables such as voltage and concentration of solution), 7) conformational fluctuations within the pore eliminated 8) temperature of the nanopore assembly can be varied over a wide range, 9) capable of metal directed self assembly with high or 100% yield, 10) height of the nanopore is far lower than protein pore (the 10 nm height of the protein channel forces several base pairs to be within the channel. This causes the electrical signatures characteristic of the base pairs to be an average over several base pairs. By using a shorter channel as in the organic nanopore approach, such averaging is avoided, permitting electrical signatures to be more representative of single base pairs. Statistical analysis can therefore be used readily to extract signatures indicative of the type of translocating nucleotide.)

The compounds of the invention may have a generally polygonal shape, such as a square when n is 4 or triangle when n is 3. The corners contain a metal atom having one or more ligands. At least one of the ligands in the entire compound is an aliphatic group. Between the metal atoms are spacers that form the edges of the polygon. When spacers are a chain of p-phenyl groups and ethyl groups and they are relatively straight and rigid. The spacers terminate in p-pyridyl groups. Suitable spacers include, but are not limited to, those shown in Eq. (4). These spacers may be made by methods known in the art. Generally, the longer the spacer, the larger the opening in the center of the compound.

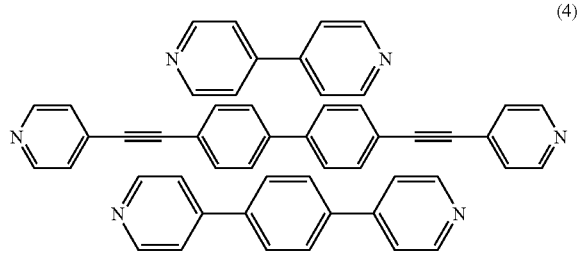

(4)

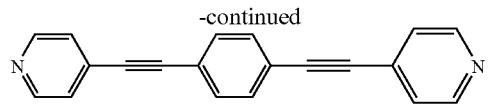

-continued

The general formula for the spacer is shown in Eq. (3). This general formula, above and as used in the claims, encompasses additional substituents on the aromatic rings, including the pyridine rings. In some embodiments, all the Ar groups are phenyl and all the substituents are hydrogen. The variable z may be the same or different in each spacer in the compound. The variables x and y may be the same or different in each repeat unit within a spacer. For example, in 1,4-bis(4-ethynylpyridine)benzene, z is 2. In one repeat unit x is zero and y is one. In the other repeat unit, both x and y are one. When all the spacers are 1,4-bis(4-ethynylpyridine)benzene, the compound is as shown in Eq. (5).

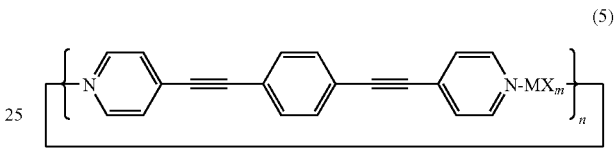

(5)

In one embodiment, the spacer is reacted with a metal compound. The metal compound contains the ligands described above, as well as a leaving group. The leaving group takes part in a reaction where a coordinative bond is formed between the metal and the nitrogen in the spacer and the leaving group is removed from the metal. Such leaving groups are known in the art. The leaving group may have a negative charge after leaving. The metal atom may also have a positive charge. The leaving group may then be the anion of a salt. Suitable leaving groups include, but are not limited to, triflate and carbon monoxide. Other counterions include, but are not limited to, nitrate, tetrafluoroborate, and hexafluorophosphate.

The metal compound may have two of the same leaving group or two different leaving groups. When the leaving group bonds in the metal compound are at a less than 180° angle to each other, the reaction can produce a cyclic compound. For example, when the leaving groups are at a right angle, then four metal compounds may react with four spacers of the same length to form a square shaped molecule.

The metal compound may also contain other ligands besides the leaving groups. Any combination of ligands, whether the same or different may be used, as long as the ligands do not prevent formation of the metal-nitrogen bond. At least one of the ligands contains an aliphatic group. Suitable ligands include, but are not limited to, trialkylphosphanyl, trioctylphosphanyl, bromide, and carbon monoxide. The ligand can comprise an aliphatic having at least 6 carbon atoms. The ligand may also be a bidentate chelating ligand including, but are not limited to, 1,2-bis(dioctadecylphosphino)ethane.

Suitable metal compounds include, but are not limited to, his(trioctylphosphino)-platinum(II)bis(trifluoromethane-sulplhonate) and pentacarbonylrhenium bromide. Another suitable metal compound is bis(trialkylphosphino)-platinum(II)bis(trifluoromethanesulphonate) or $Pt(PR_3)_2(OSO_2CF_3)_2$ where each R group is independently selected. Two example compounds are shown in Eq. (6). These compounds may be in equilibrium with each other.

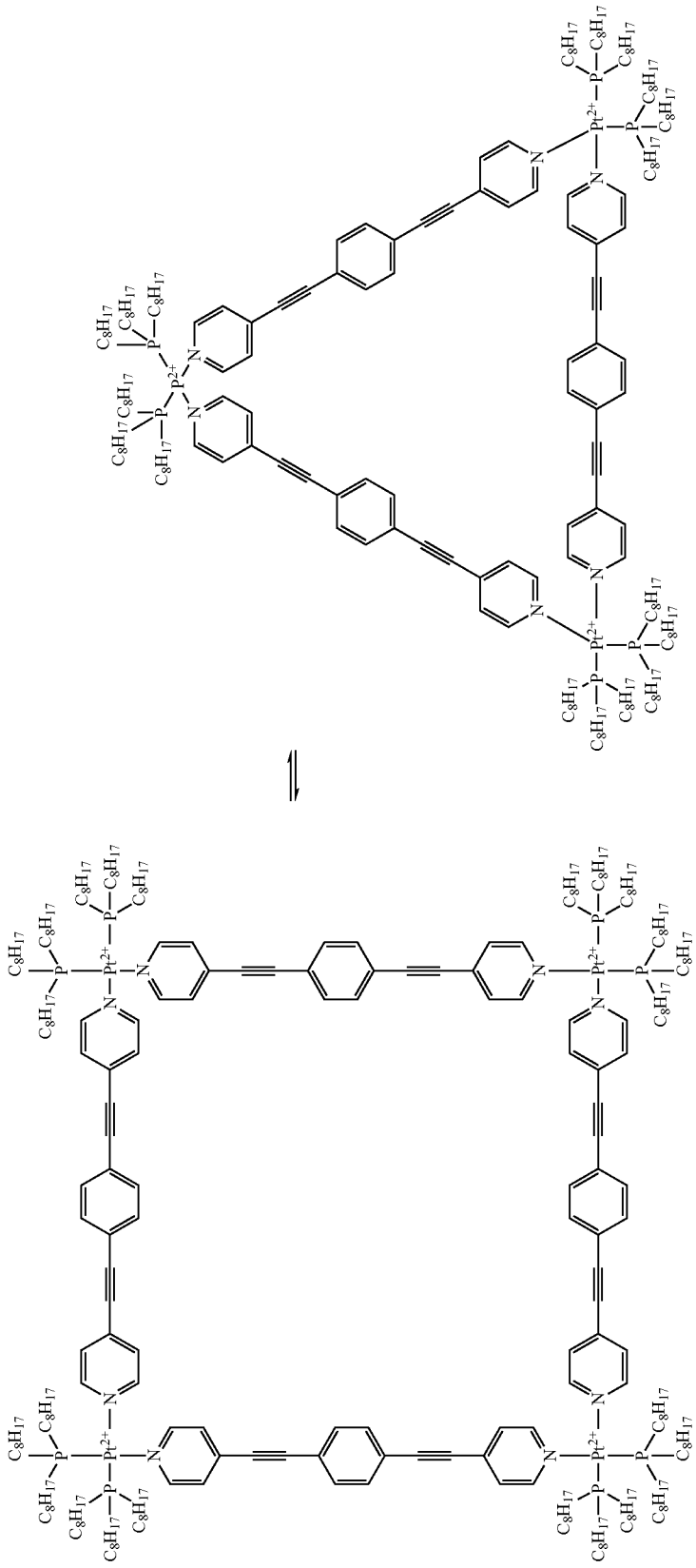

The compound may be made with all identical spacers and identical metal compounds. Alternatively, combinations of different spacers and metal compounds may be used within one compound. The different elements may be randomly arranged, or they may form a regular pattern. In one embodiment, a compound having two different corner groups is made, where opposite corners have the same group. This may be done in a two-step reaction. In the first step, a spacer is reacted with a metal compound in a 2:1 molar ratio. The product contains two spacers bonded to the metal atom, and may form a right angle. This intermediate is then reacted with another metal compound in an equimolar ratio. In this reaction, the two light angle compounds form a complete square. An example of this type of compound is shown in Eq. (7).

Application to Shenoy et al., "Method of Stabilization of Functional Nanoscale Pores for Device Applications," designated as N.C. 96,168, and filed on the same day as the present application (incorporated herein by reference). The solubility may be enhanced by the aliphatic ligands. A long chain aliphatic, such as octyl, may be rapidly soluble in the long aliphatic chains of lipids. The compound may form a pore through the membrane. This structure may be useful for DNA and other polynucleotide sequencing. An electrolyte solution containing the DNA is placed on one side of the membrane. Electrolyte is also placed on the other side of the membrane. A voltage is applied through the electrolytes and across the membrane. This causes a DNA strand to gradually pass through the membrane. As the strand passes through, the

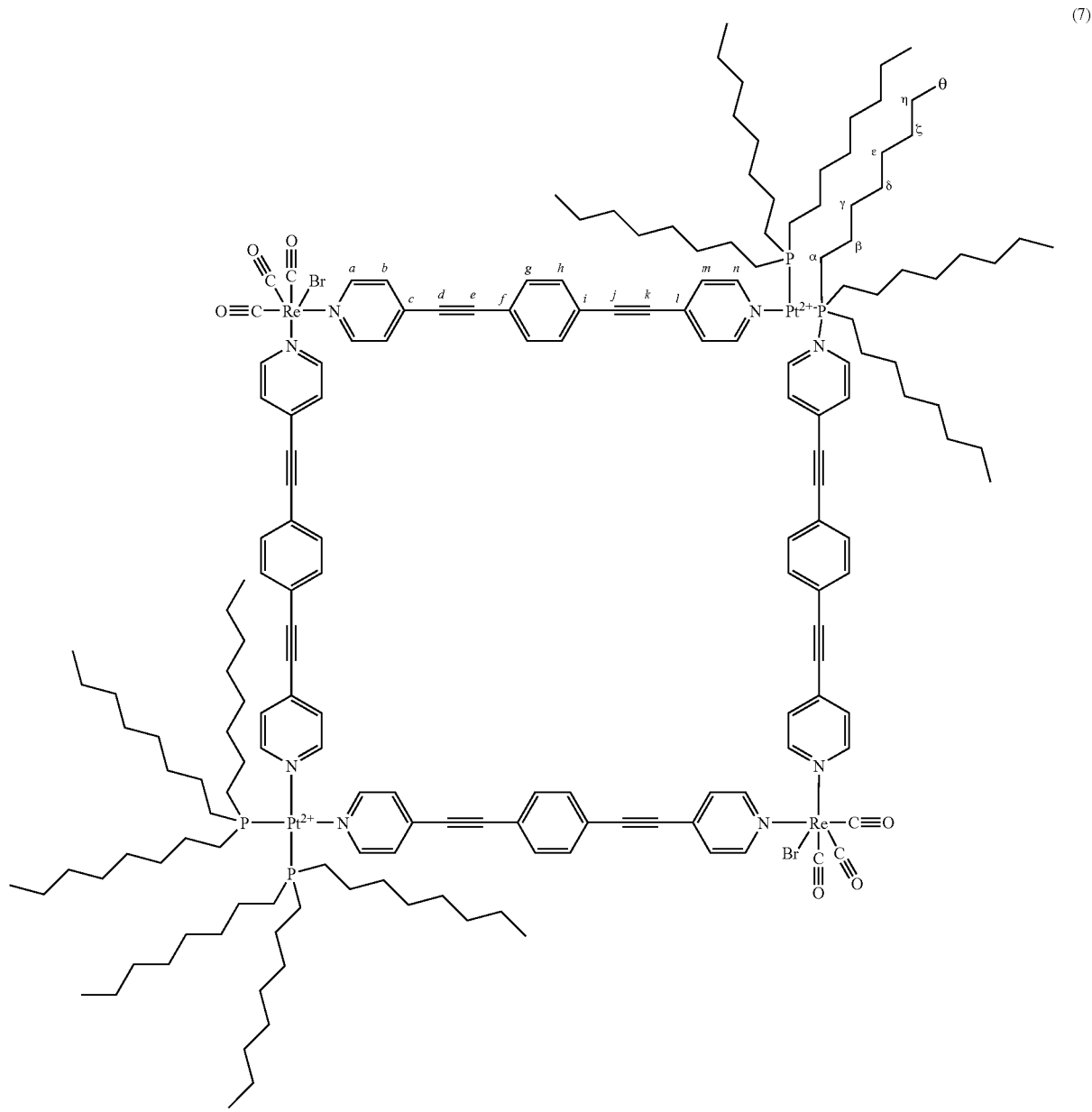

(7)

The compound may be soluble in a lipid membrane, including the black lipid membranes disclosed in U.S. Patent current passing through the membrane is measured. The current is affected by the number and identity of the nucleotides presently in the pore. When using protein ion channels, there is typically more than one nucleotide in the pore. The identity of each nucleotide is determined from several current measurements as the nucleotide passes through the pore. A synthetic pore may be short enough to hold only one nucleotide. This simplifies the sequencing, as each nucleotide identification is determined from a single current measurement.

This approach may enable high selectivity, sensitivity, and real-time molecular recognition for a variety of target molecules of interest such as DNA, RNA, proteins, and ions. The proposed method can have the potential to sequence single stranded DNA (ssDNA) and RNA with resolution at the single base level, with similar capabilities for proteins (at the single amino acid level) and individual ions.

The compounds may enable modification of the interaction forces at the molecular level through molecular engineering of the organic nanopore. This ability translates into a handle on the translocation of biomolecules (residence time of base pairs within the pore can be controlled) with potential for single base pair resolution. Further, information on the effect of interferents such as small molecules, ions etc may be obtained. Similar resolution may be realized for proteins for amino acid sequencing and for ions such as for Ca channels. Also, since the organic nanopores can be robust, it may be possible to investigate the effects of translocation at higher temperatures. The enhanced diffusion rates at higher temperatures may allow for higher throughput sequencing to be achieved.

Having described the invention, the following examples are given to illustrate specific applications of the invention. These specific examples are not intended to limit the scope of the invention described in this application.

EXAMPLE 1

Synthesis of 1,4-bis(4-ethynylpyridine)benzene—This dipyridine spacer compound has been reported in the literature (Champness et al., "An Improved Preparation of 4-Ethynylpyridine and its Application to the Synthesis of Linear Bipyridyl Ligands," *Tetrahedron Lett.*, 40, 5413-6416 (1999)) and was prepared according to known literature procedures. 400 mg of 4-ethynylpyridine hydrochloride (2.87 mmol), 451 mg of 1,4-diiodobenzene (1.37 mmol), 20 mg of bis(triphenylphosphino)palladium(II)dichloride (0.028 mmol), and 7 mg of copper(I)bromide were suspended in 10-15 mL of triethlyamine and heated to 60"° C. for 1 hour while stirring vigorously. Then the mixture was heated further and kept at reflux temperature for 48 hours, Subsequently the triethylamine was removed by evaporation under reduced pressure. The residue was dissolved in dichloromethane (100-200 mL) and the resulting dark solution was washed with 100 mL of a saturated aqueous solution of dipotassium carbonate. The dichloromethane fraction was then dried over disodium sulphate, filtered, and evaporated under reduced pressure. The resulting crude, dark reaction product was purified by column chromatography ($SiO_2$, eluent: ethylacetate/hexane/dichloromethane 2/1/3, the product was photoluminescent upon irradiation with UV light). Yield 150 mg (40%).

Characterization: $^1$H NMR (300 MHz, $CDCl_3$, 300K), δ (ppm): 8.61 (d broadened, J=4.4 Hz, 4H; $H_a$), 7.56 (s broad, 4H; $H_g$), 7.10 (m broadened, $J_1$=4.4 Hz, 4H; $H_b$).

EXAMPLE 2

Synthesis of 4,4'-bis(ethynyl-4-pyridine)biphenyl—this spacer was synthesised by the same procedure as applied in Example 1 using 4,4'-diiodobiphenyl instead of 1,4-diiodobenzene.

Characterization: $^1$H NMR (300 MHz, DMSO-$d_6$, 300K), δ (ppm): 8.62 (d broadened, J=6.0 Hz, 2H; $H_a$), 7.84 (d broadened, J=8.5 Hz, 2H; $H_h$), 7.71 (m broadened, $J_1$=8.5 Hz, 2H; $H_b$), 7.53(m, $J_1$=6.0 Hz, 2H; $H_g$); $^{13}$C{$^1$H} NMR (75 MHz, $CDCl_3$, 300K), δ (ppm): 150.6 (s, 4C; $C_a$), 141.6 (s small; $C_i$), 133.2 (s, 4C; $C_h$), 132.1 (s small; $C_c$), 127.9 (s, 4C; $C_b$), 126.3 (s, 4C; $C_g$), 122.4 (s small; $C_f$), 94.4 (s small; $C_d$), 88.5 (s small; $C_e$).

EXAMPLE 3

Synthesis of bis(trioctylphosphino)-platinum(II)bis(trifluoromethanesulphonate)—This compound was obtained by replacing the chloride ions of bis(trioctylphosphino)platinumdichloride with trifluoromethylsulphonate ions ($CF_3SO_3^-$, also known as 'triflate'). 57 mg of bis(trioctylphosphino)platinum(II)dichloride (0.057 mmol) were dissolved in 10 mL of dichloromethane. 29.1 mg of silver(I)trifluoromethanesulphonate (0.113 mmol) were added and the solution was stirred for about 1 hour under exclusion of light. The white precipitate (silver(I)chloride) was filtered off and the solution was evaporated under reduced pressure. Yield: 68 mg (97%).

EXAMPLE 4

Synthesis of Compound in Eq. (6)—1,4-Bis(4-ethynylpyridine)benzene and bis(trioctylphosphino)platinum-bis(trifluoromethylsulphonate) were mixed in equimolar amounts in a chloroform solution. The two forms (square and triangle) were in a dynamic equilibrium in solution, with a square:triangle ratio of 3:7. In the square, the distance from one corner to the opposite corner was 2.2 nm. In the triangle, distance from one corner to the opposite edge was 1.7 nm. The solid state composition of the assemblies is unknown.

Characterization: $^1$H NMR (300 MHz, $CDCl_3$, 300K), δ ppm: spacer:square) 9.35 (d broad, J=5 Hz, 16H; $H_a$), 7.65 (m, broad, partially below signals of triangle, 16H; $H_b$), 7.51 (m, partially below signals of triangle, 16H; $H_g$); triangle) 9.32 (d, broad, J=5 Hz, 16H; $H_a$), 7.60 (d, J=6 Hz, 16H; $H_b$), 7.51 (s, broad, 16H; $H_g$); phosphine alkyl chains for square and triangle: (1.7, m, very broad, ~96H; $CH_2$ α and β), 1.2 (s, very broad, ~240H; $CH_2$ γ-η), 0.85 (t broad, J≈5 Hz, ~72H; $CH_3$ θ); $^{31}$P NMR (161.98 MHz, $CDCl_3$, 300K), δ ppm: −13.84 ($^1$J coupling with $^{195}$Pt (33.8% abundance): 3122). (Subscripts a-n and α-θ are as in similar compound in Eq. (7).)

EXAMPLE 5

Synthesis of bis(1,4-bis(ethynyl-4-pyridine)benzene)rhenium(I)tricarbonylbromide—9.9 mg of pentacarbonylrhenium bromide (Re(CO)$_5$Br, 0.024 mmol) and 15.0 mg of 1,4-bis(4-ethynylpyridine)benzene (0.054 mmol) were heated in isooctane at 60° C. for 36 hours. The formed precipitate was filtered (or decanted) and was washed once with 3-4 mL of isooctane. After drying under high vacuum the resulting product was found to be >95% pure by $^1$H NMR. Yield: 95%.

Characterization: $^1$H NMR (300 MHz, CDCl$_3$, 300K), δ ppm: 8.81 (d, J=6.6 Hz, 4H; H$_a$), 8.64 (d, J=6.0 Hz, 4H; H$_e$), 7.59 (s, broad, 8H; H$_g$ and H$_h$), 7.44 (d, J 6.0 Hz, 4H; H$_m$), 7.40 (d, J=6.6 Hz, 4H; H$_b$).

EXAMPLE 6

Synthesis of Compound in Eq. (7)—The compound was prepared by mixing bis(spacer)rhenium(I)tricarbonylbromide ((spacer)$_2$Re(CO)$_3$Br) and bis(trioctylphosphino)-platinum(II)bis(trifluoromethanesulfonate) in equimolar amounts in a chloroform solution. The compound was soluble in dimethylsulfoxide (DMSO), and slightly soluble in chloroform or acetone. The distance from one corner to the opposite corner was 2.2 nm. Molecular weight: 4287.5 g/mole.

Characterization: $^1$H NMR (300 MHz, CDCl$_3$, 300K), δ ppm: 9.35 (s, broad, 8H; H$_n$), 8.79 (s, broad, 4H; H$_e$), 7.66-7.51 (m, 16H; H$_g$ and H$_h$), 7.54 (s, broad, 8H; H$_m$), 7.39 (s, broad, 8H; H$_b$), 1.94 (s, very broad, 24H; PR$_3$ H$_α$), 1.63 (s, very broad, 48H; PR$_3$ H$_β$ and H$_γ$), 1.26 (s, very broad, 96H; PR$_3$ H$_δ$ to H$_n$), 0.87 (s, broad, 36H; PR$_3$ methyl H$_θ$). (Subscripts a-n and α-θ are as in Eq. (7).)

EXAMPLE 7

Figure 2:
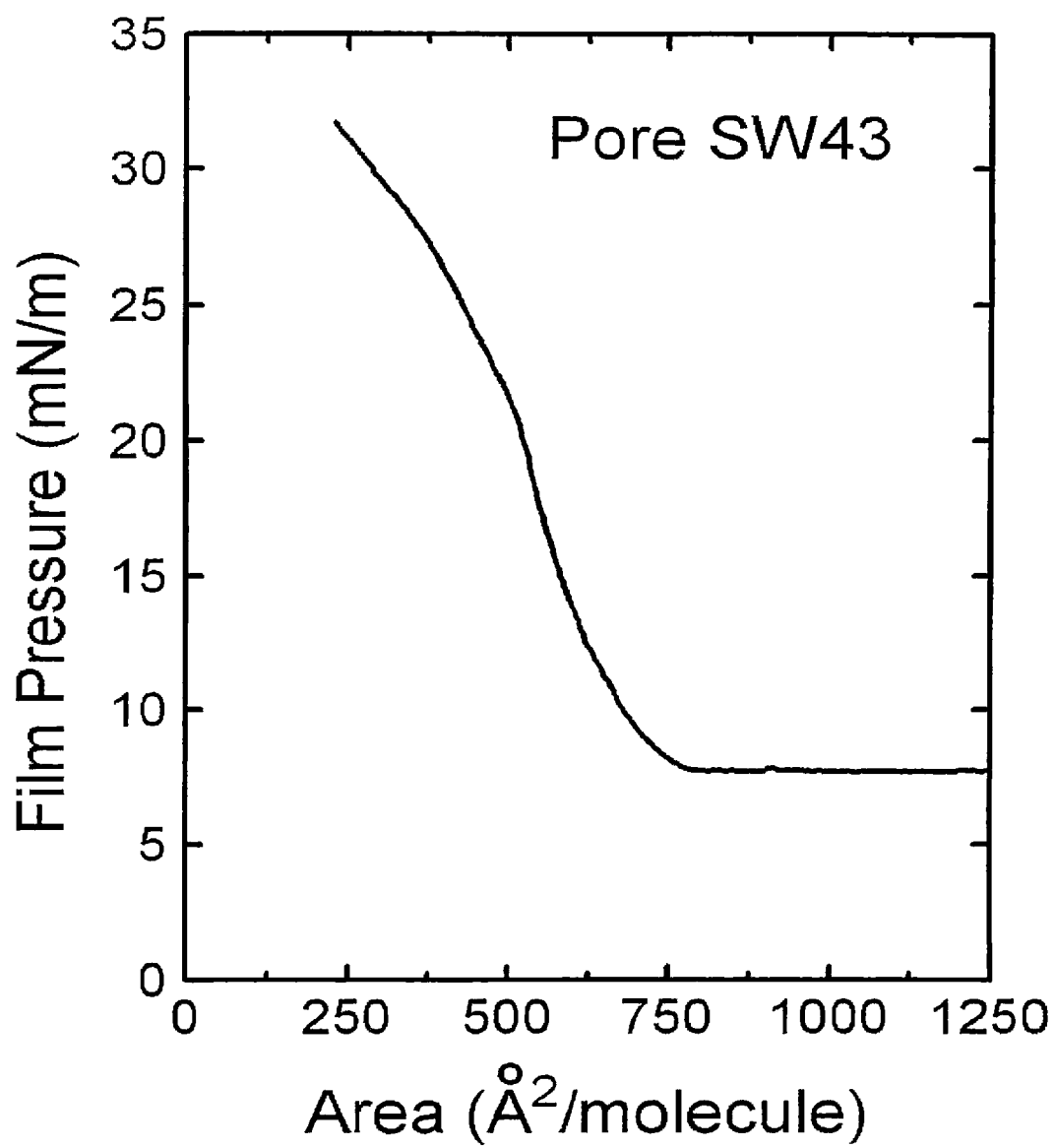
FIG. 2 shows a Langmuir Blodgett isotherm of a pure nanopore compound.

Nanopore-Lipid Compatibility Experiments—To demonstrate that the synthetic nanopore will partition into lipid membranes to form single channels, Langmuir Blodgett (LB) isotherms were generated of the pure nanopore material as well as mixtures of nanopores and lipids. FIG. 2 shows an example of an isotherm from which the cross-sectional area of the pore was calculated. The calculated size agrees with the size computed based on molecular structure and is large enough for single stranded DNA translocation. Further, this LB experiment also proved that the pore is oriented with the channel axis parallel to the long axis of the phospholipid molecules.

Obviously, many modifications and variations of the present invention are possible in light of the above teachings. It is therefore to be understood that the claimed invention may be practiced otherwise than as specifically described.

What is claimed is:

1. A lipid membrane comprising a compound having the formula:

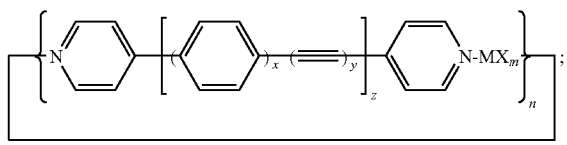

wherein each M is independently selected from the group consisting of palladium, platinum, and rhenium;

wherein each X is an independently selected from the group consisting of trialkylphosphanyl, 1,2-bis(dioctadecylphosphino)ethane, bromide, and carbon monoxide, with the proviso that at least one X in the compound is trialkylphosphanyl;

wherein each x, each y, and each z is an integer greater than or equal to zero;

wherein each m is an integer greater than or equal to one; and wherein n is an integer greater than or equal to three.

2. The lipid membrane of claim 1, wherein the compound has the formula:

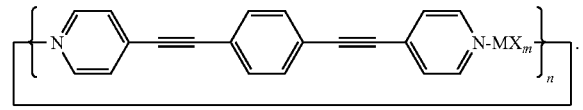

3. The lipid membrane of claim 1, wherein n is selected from the group consisting of 3 and 4.

4. The lipid membrane of claim 1, wherein the compound has the formula:

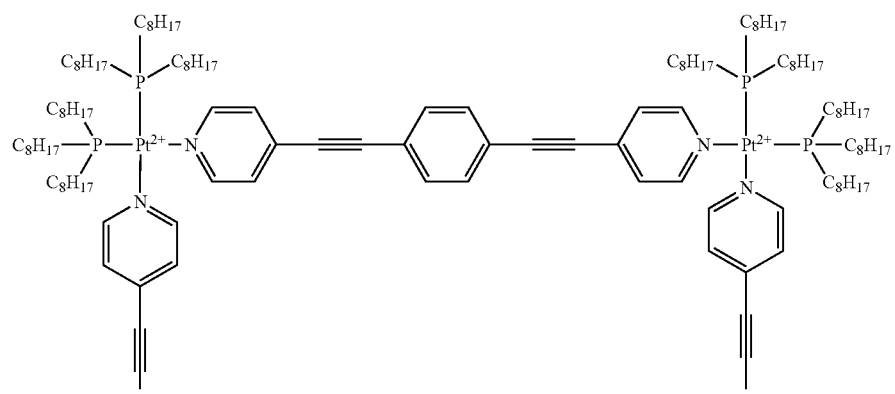

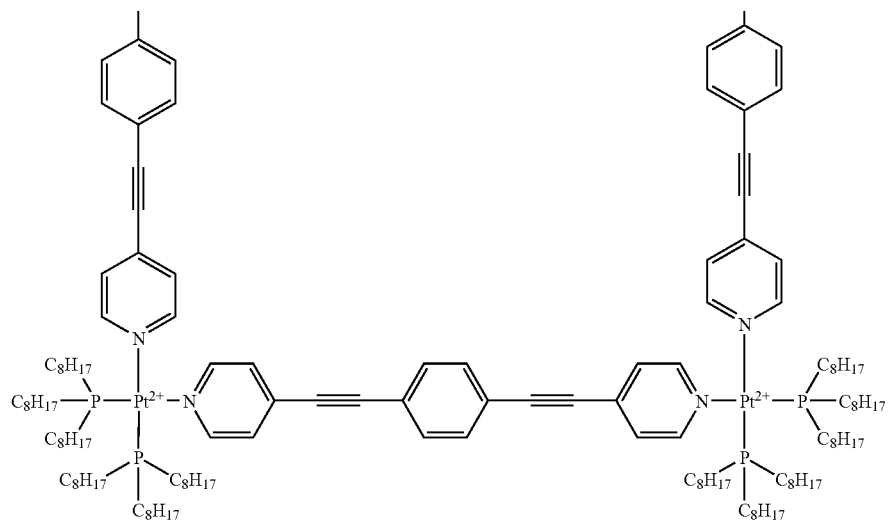
5. The lipid membrane of claim 1, wherein the compound has the formula:
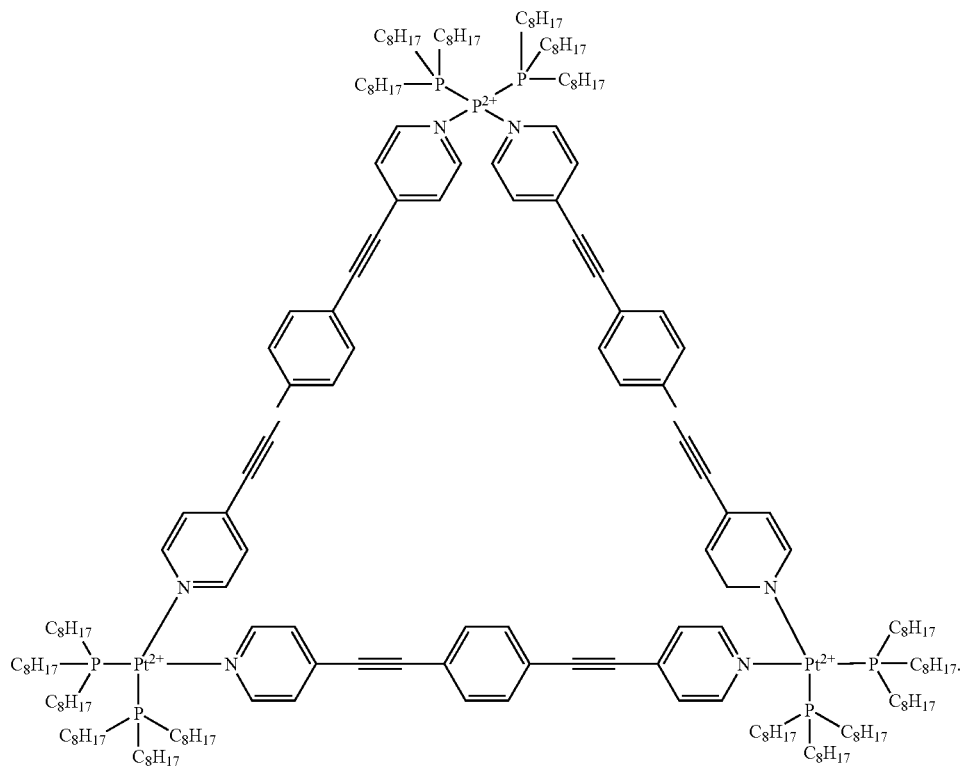

6. The lipid membrane of claim 1, wherein the compound has the formula:
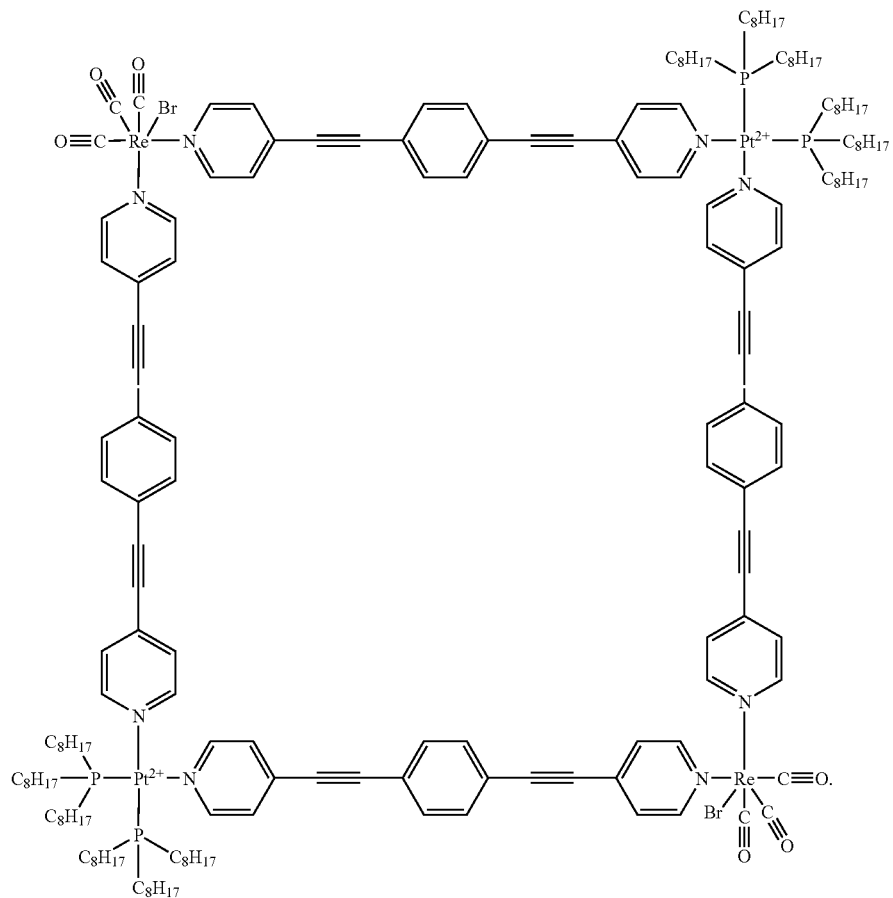
40
7. The lipid membrane of claim 1, wherein X is trioctylphosphanyl.
* * * * *